United States Patent
Wang et al.

[11] Patent Number: 5,992,216
[45] Date of Patent: *Nov. 30, 1999

[54] METHOD TO ANALYZE PARTICLE CONTAMINANTS IN COMPRESSED GASES

[75] Inventors: Hwa-chi Wang, Downers Grove; Richard J. Udischas, Chicago, both of Ill.

[73] Assignee: American Air Liquide Inc., Walnut Creek, Calif.

[ * ] Notice: This patent is subject to a terminal disclaimer.

[21] Appl. No.: 08/865,104

[22] Filed: May 29, 1997

Related U.S. Application Data

[62] Division of application No. 08/240,485, May 10, 1994, Pat. No. 5,665,902.

[51] Int. Cl.⁶ ............................................. G01N 1/00
[52] U.S. Cl. ...................... 73/28.01; 73/31.03; 73/865.5
[58] Field of Search ................... 73/28.01, 863.11, 73/863.12, 31.03, 865.5

[56] References Cited

U.S. PATENT DOCUMENTS

| | | | |
|---|---|---|---|
| 3,892,549 | 7/1975 | Lyschkow | 73/28.04 X |
| 4,154,088 | 5/1979 | Werner | 73/28.01 |
| 4,704,804 | 11/1987 | Wyatt et al. | 34/15 |
| 4,878,510 | 11/1989 | Kaspar et al. | 137/1 |
| 4,912,985 | 4/1990 | Daum et al. | 73/863.25 |
| 4,964,278 | 10/1990 | Wen et al. | 62/55.5 |
| 5,026,155 | 6/1991 | Ockovic et al. | |
| 5,027,642 | 7/1991 | Wen et al. | 73/23.2 |
| 5,101,671 | 4/1992 | Elgas | 73/863.23 |
| 5,190,726 | 3/1993 | Shinoke et al. | 422/62 |
| 5,209,102 | 5/1993 | Wang et al. | 73/28.01 |
| 5,214,952 | 6/1993 | Leggett et al. | 73/31.03 X |
| 5,519,490 | 5/1996 | Nakata et al. | 356/338 |
| 5,673,562 | 10/1997 | Friedt | 62/48.1 |

Primary Examiner—Hezron Williams
Assistant Examiner—Jay L. Politzer
Attorney, Agent, or Firm—Burns, Doane, Swecker & Mathis, L.L.P

[57] ABSTRACT

A system and a method for analyzing impurities in compressed gas, a method for controlling the particle growth in the monitored gas and a method for determining the optimum monitoring temperature for an individual gas are disclosed.

14 Claims, 6 Drawing Sheets

METHOD TO ANALYZE PARTICLE CONTAMINANTS IN COMPRESSED GASES

This application is a divisional, of application Ser. No. 08/240,485, filed May 10, 1994, U.S. Pat. No. 5,665,902

BACKGROUND OF THE INVENTION

1. Field of the Invention

The present invention relates to a system and a method for analyzing particles in compressed gases, a method for controlling the particle growth in the system and a method for determining the optimum temperature for individual gases under various conditions.

2. Description of Related Art

Continuous monitoring of particles in bulk distribution systems is common practice and extremely low particle levels are required. Similarly, there is a need to quantify and verify particle concentration in cylinder gases. However, the true particle content of compressed cylinder gases is more difficult to determine for several reasons. Full cylinder pressure is typically about 20 times greater than that of a pipeline. The increased pressure makes pressure reduction for particle sampling more difficult. Additionally, the pressure in a gas cylinder decreases with usage, which affects the detected particles. Thus, sampling techniques used for pipeline gases are not directly applicable to cylinder gases. Moreover, there are sampling artifacts associated with cylinder gas pressure reduction.

Particle detection and analysis in chemical gases is important in the microelectronics industry. The requirements of such particle counters were discussed by Wang and Udischas (Microcontamination 93 Conference Proceedings, pp. 465–472), which is incorporated herein by reference in its entirety. The three specific requirements for such particle counters are material compatibility, purgability, and operating pressure. One of the key requirements is to measure particles at full cylinder pressure which may be the saturated vapor pressure for gases packaged in the liquid phase, such as HCl, or at the supercritical state for gases packaged in the gas phase, such as $CF_4$.

A pressure-balancing technique was developed by Wang and Udischas (U.S. Pat. No. 5,209,102, issued May 1993, which is incorporated herein by reference in its entirety) to prevent the negative effects of particle bursts associated with the opening of the cylinder valves. This particle sampling and analysis technique was implemented in Air Liquide filling centers and was used to optimize cylinder filling processes (Air Liquide Electronics Journal, December 1993, which is incorporated herein by reference in its entirety).

However, molecular clusters and nanometer particles undergo extremely frequent collisions with other molecules, clusters, or particles. The sticking probability after collision determines if and how the clusters and particles grow. The predictive equations for the sticking probability between nanometer particles and wire screens were given by Wang (Eqn. 6–8, Aerosol Sci. Tech., 18, 180–186, 1993, which is incorporated herein by reference in its entirety).

Field tests show high particle concentrations for many gases at a saturated vapor pressure or supercritical state. The particle counts remain roughly the same even when a high efficiency particle filter is placed upstream of the particle counter (See FIG. 1). This indicates that the registered particles are artifacts associated with particle formation from molecular clustering and/or condensation of vapor-phase species. Because of the high concentration of these artifact particles, the true particle contaminants in the chemical gases are masked and cannot be easily determined.

The art lacks a system and a method for analyzing these particle contaminants in gases, including gases at a saturated vapor pressure or supercritical state. The art also lacks a method for reducing the artifacts associated with particle formation from molecular clustering and/or condensation of vapor-phase species.

SUMMARY OF THE INVENTION

In accordance with one aspect of the present invention, there is provided a system for analyzing particles in compressed gas. The system includes a source of compressed gas, a sensor for measuring particle impurity within the gas, a temperature controller for controlling the temperature of the gas to eliminate particle formation from molecular clustering and condensation, and a pressure balancer.

More specifically, the system includes a first valve located between the compressed gas source and the sensor, a second valve for introducing the gas to the system, a filter located downstream from the second valve for substantially removing particle impurities in the source gas and/or introduced by the upstream components, a third valve located downstream from the filter for controlling the initial exhaust of the gas from the system after pressure balancing, an orifice located between the filter and sensor for back-filling the gas to the sensor until there is a pressure equilibrium across the first valve and also for controlling the exhaust flow rate, and a temperature zone regulated by a temperature controller and located between the orifice and the sensor for controlling the temperature of the gas to eliminate particle formation from molecular clustering and condensation.

In accordance with another aspect of the present invention, there is provided a method for analyzing particles in compressed gas at elevated pressure, including introducing a compressed gas into a particle sensor, regulating the pressure of the gas, and maintaining the temperature of the gas at a predetermined value while monitoring the particle count.

In accordance with a further aspect of the present invention, there is provided a method for determining the optimum temperature for analyzing the particle content of a compressed gas at a given pressure which includes introducing a compressed gas at a first pressure and a first temperature through a filter to a particle sensor, monitoring the particle count of the gas, and incrementally increasing the temperature while monitoring the particle count until the particle count approaches a minimum.

BRIEF DESCRIPTION OF THE DRAWINGS

Other objects, features and advantages of the present invention will become apparent from the following detailed description and accompanying drawings wherein.

DETAILED DESCRIPTION OF PREFERRED EMBODIMENTS

The present invention provides a system and a method for analyzing particles in compressed gases. The particles are detected in a wide variety of cylinder gases. The present invention includes a method for controlling the particle growth in the system and a method for determining the optimum temperature for an individual gas under various conditions.

The system and method of the present invention can detect particle concentrations for a wide variety of cylinder gases, including those at saturated vapor pressure or supercritical state. The method effectively reduces the artifacts associated with particle formation from molecular clustering or condensation of vapor-phase species. The true particle contaminants in the chemical gases would otherwise be masked by the high concentration of these artifact particles, making detection difficult.

Particle formation from molecular clustering or condensation is eliminated by the lowering of the sticking probability. This effect is achieved by the present invention by modifying the operating conditions during analysis of the gas. By controlling the temperature the sticking probability is reduced thereby reducing the particle growth process.

A wide variety of compressed gases are suitable for use in the present invention. Suitable gases include electronic specialty gases ("ESG"), which are typically contained in gas cylinders at a wide range of pressures up to 3000 pounds per square inch ("psi") (200 bar). Metallic impurities in ESG's are of critical concern in micro-electronics manufacturing processes. Suitable gases include inert gases, such as $N_2$, Ar, He, and the like; etchant gases, such as $Cl_2$, HCl, $BCl_3$, HBr, $SF_6$, $CF_4$, $C_2F_6$, and the like; and reactive gases, such as $SiH_4$, $SiH_2Cl_2$, $NH_3$, other gases compatible with system materials, and the like.

The preferred temperature setting depends on the type of gas, the cylinder pressure, and the withdrawn flow rate. The temperature setting is directly related to the withdrawn flow rate. The higher the flow rate, the higher the temperature setting that is required to evaporate the artifact particles. The preferred temperature setting can be determined individually as described below for each application, and preferably does not exceed 250° C. The temperature is set at a predetermined preferred temperature and the system is allowed to reach equilibrium at the intended sampling flow rate prior to actual sampling.

Figure 2:
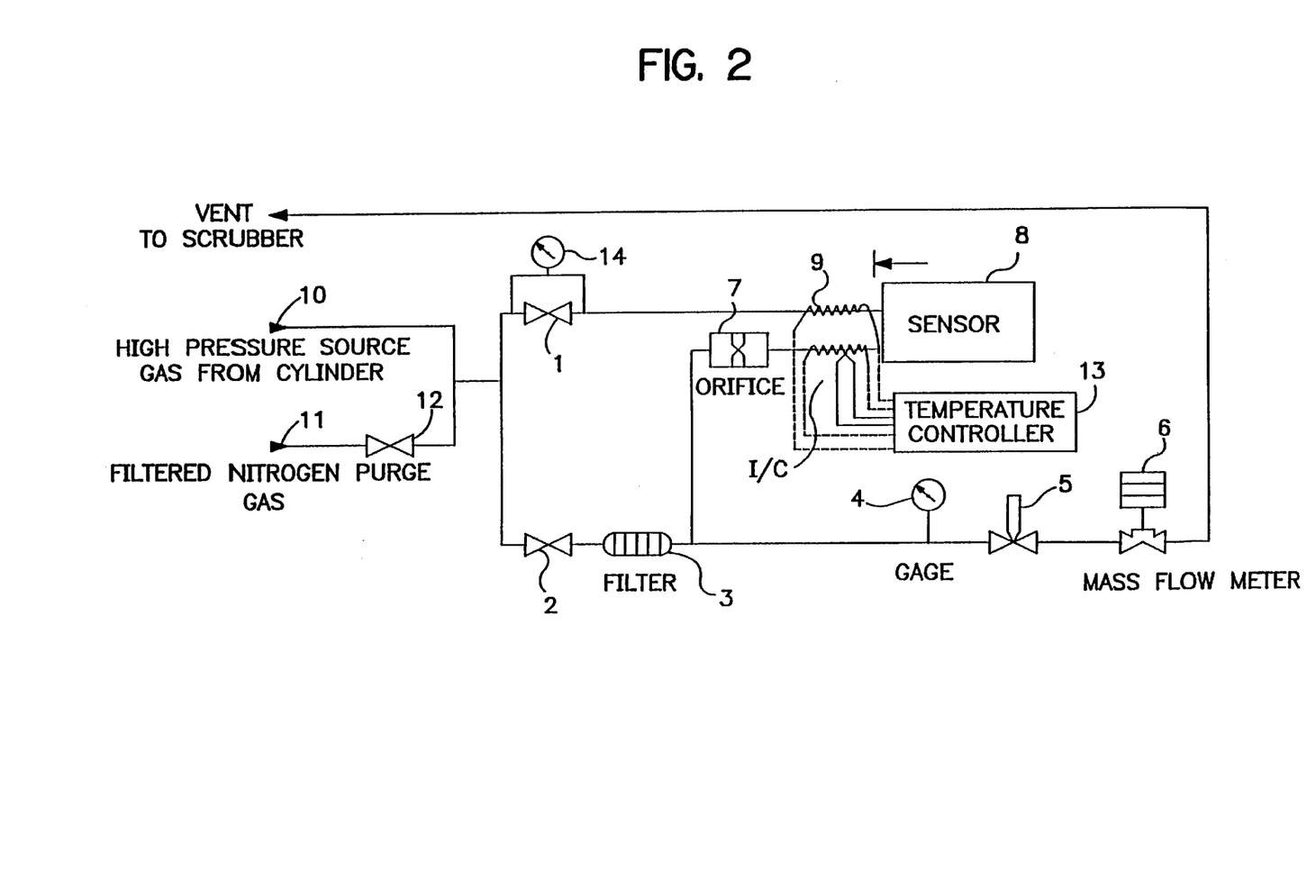
FIG. 2 is a schematic illustration of the system of the present invention.

A temperature control device is provided in combination with the pressure-balancing device described in U.S. Pat. No. 5,209,102, which is incorporated herein by reference in its entirety, as shown in FIG. 2. Referring to FIG. 2, two operational modes are contemplated in employing such a system, i,e., the purge mode and sample mode. In the purge mode, two flow paths are available for a complete purge of the system. The first flow path includes a valve 12, a valve 1, an impurity sensor 8, a temperature zone 9 connected to a temperature controller 13, an orifice 7, a pressure gauge 4, a valve 5 and a flow meter 6. The flow of the first path is controlled by the orifice 7 and the volume of flow indicated by the flow meter 6.

The second flow path of FIG. 2 includes the valve 12, a valve 2, a filter 3, the pressure gauge 4, the valve 5 and the flow meter 6. The flow of the second path is controlled by a valve 6, which typically is greater than the flow of the first path because the large surface area of a filter 3 requires high purge flow.

It is contemplated that each flow path be first purged either sequentially or simultaneously by a purge gas 11. Purge gases should be purified and filtered and comprise such inert gases as nitrogen, argon and helium.

It is contemplated that before gas sampling begins, pressure balance is established. In doing so, the valve 1 which controls gas flow to the sensor is first closed. A source gas 10 at cylinder pressure is introduced to the back-filling leg. It is noted that because of the closure of the valve 1, the sensor is isolated from pressure surges introduced by the cylinder source gas 10 as well as contaminants introduced by the valve 2 as the filter 3 is employed downstream of the valve 2.

After the pressure balance stage, the majority of flow of the source gas is exhausted from the system at a flow rate which is controlled by the valve 5. This flow rate is indicated by the flow meter 6 which can be, for example, a mass flowmeter or rotameter. The pressure gauge 4, upstream of the valve 5, provides the user with the pressure of the source gas 10.

During the pressure balancing process, flow of the source gas 10 is caused to pass through the orifice 7 to back-fill the sampling leg. Back-filling continues until the pressures on both sides of the control valve 1 are balanced. The time required to reach pressure balance can be determined either by direct measurement or by calculation. Direct measurement is accomplished by employing a differential pressure gauge (not shown) located across the control valve 1. However, the installation of a differential pressure gauge introduces dead spaces just before the sensor which require a dedicated procedure to purge. Alternatively, one can estimate the time required to reach pressure balance by a semi-empirical equation (See U.S. Pat. No. 5,209,102, issued May 1993, which is incorporated herein by reference in its entirety).

After pressure balance is reached by back-filling, sampling can be started by opening the control valve 1 for the sampling leg and closing the control valve 2 for the back-fill leg. Flow of the source gas 10 is now directed through the sensor 8 and the temperature zone 9 of the temperature controller 13 at the same pressure as the source gas and flow is controlled by the orifice 7. The temperature of the gas is maintained at the preferred temperature setting for the actual sampling pressure and flow rate used. The preferred temperature is the temperature which eliminates the artifact particles. As a preferred embodiment, the orifice can be used to control sampling flow through the sensor. The diameter of the orifice is determined by the specific residence time of the sensor.

The actual flow rate of the source gas 10 passing through the sensor 8 will obviously decrease with decreasing pressure. The flow rate at any particular time can be determined simply by referencing the flow meter 6. The total sample volume can be easily obtained by integrating the indicated flow rate over the sampling period.

Figure 6:
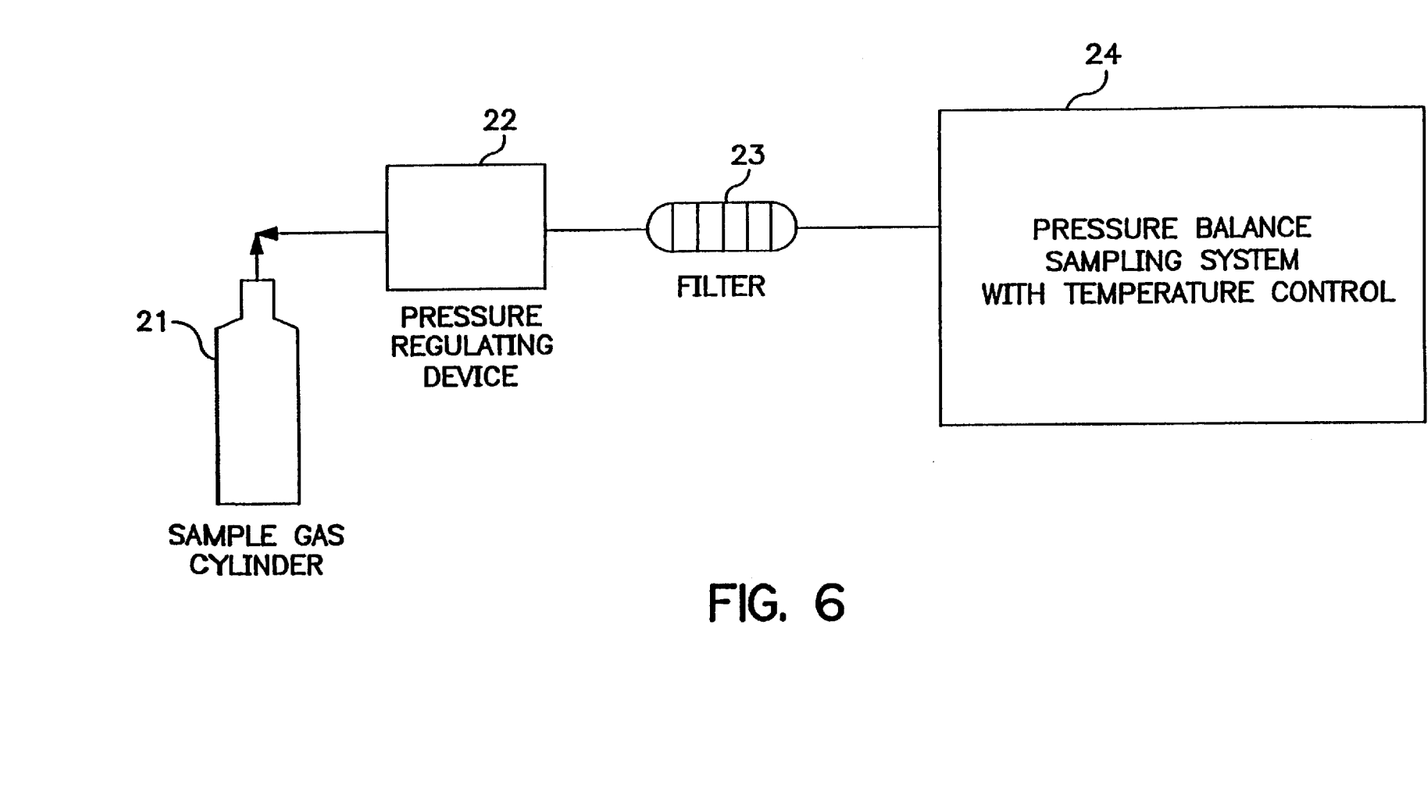
FIG. 6 is a schematic illustration of the system of the present invention for determining the optimum temperature for an individual gas.

The system of the present invention can determine the preferred temperature setting for a given gas at various pressures. The microstructure of gases at supercritical state is poorly understood and therefore no equations are available to calculate the preferred temperature. However, the preferred temperature can be experimentally determined as follows. The method can be generally applied for all gases compatible with a particle counter. Referring to FIG. 6, one embodiment of the system is shown wherein a sample gas cylinder 21 is connected to a pressure regulating device 22. The pressure of the exit gas is regulated and the gas is passed through a filter 23 prior to entering a pressure-balance temperature-control sampling system 24. The particle filter downstream of the pressure regulator removes all particles from the cylinder gas and from the flow handling components, such as the cylinder valve and the pressure regulator. After proper purging, the sample gas is regulated and introduced through the filter into the pressure-balancing, temperature-controlled system during particle counting. Suitable purge gases include nitrogen, argon, helium, and the like.

Starting from near ambient pressure, a minimum of particle counts is established. The pressure is then increased incrementally until the onset of additional particle counts occurs. At the onset pressure, the temperature is then increased incrementally. The increase of the temperature should be slow to allow equilibrium of the whole system. At each temperature, particle counts are recorded and should follow a decaying trend with increasing temperature. The preferred temperature setting for this pressure is the temperature at which the particle counts reach a minimum. A further increase of pressure requires a further increase of the temperature setting to obtain minimum counts. By repeating this process, the preferred temperature setting at each pressure is established.

EXAMPLE 1

A cylinder of $CF_4$ at full cylinder pressure was measured for particle concentration. The gas at the supercritical state was released from the cylinder and measured in a pressure balance sampling system for particle concentration for 30 minutes. The results are shown in FIG. 1 and the data is indicated by the "no filter" notation and show high particle concentrations for the gas at the supercritical state.

Figure 1:
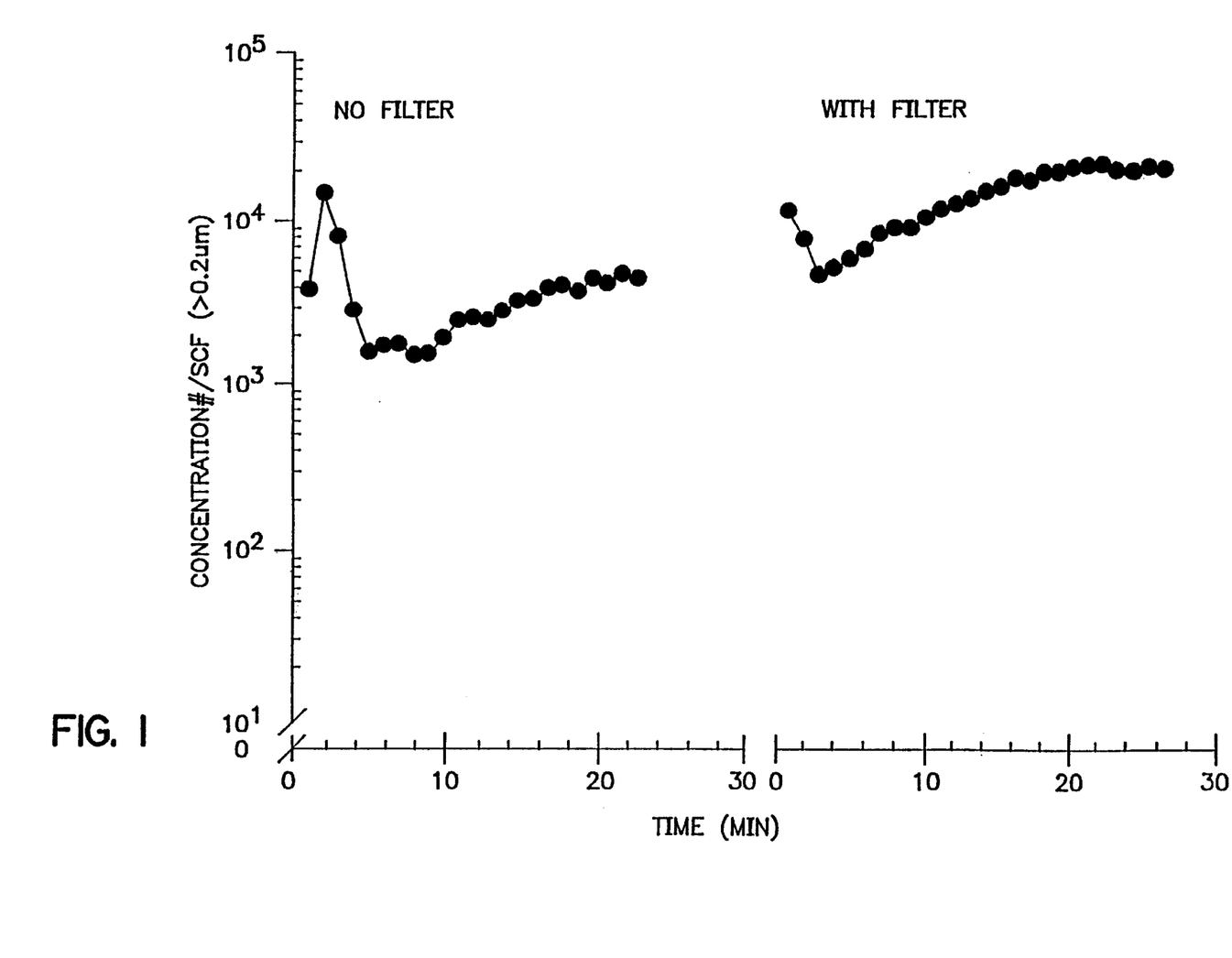
FIG. 1 is a graph exhibiting the relationship between the $CF_4$ particle concentration at full cylinder pressure over time with and without a particle filter placed upstream of the particle counter.

The particle counts remain roughly the same even when a high efficiency particle filter is placed upstream of the particle counter (See FIG. 1 data "with filter").

A comparison of these results indicates that the registered particles are artifacts associated with particle formation from molecular clustering or condensation of vapor-phase species. Because of the high concentration of these artifact particles, the true particle contaminants in the chemical gas are masked and cannot be easily determined.

EXAMPLE 2

Figure 3:
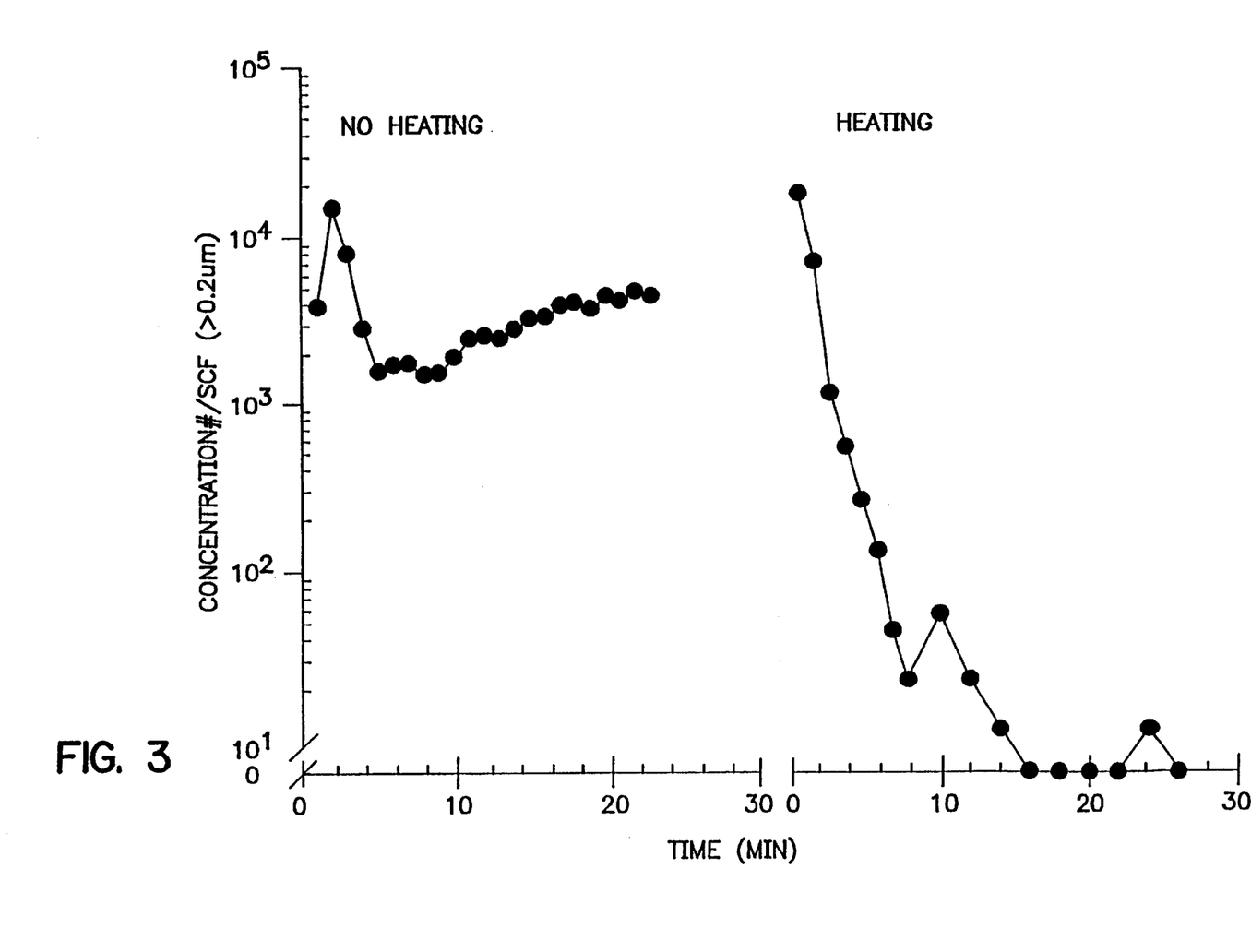
FIG. 3 is a graph exhibiting the relationship between the $CF_4$ particle concentration at full cylinder pressure over time with and without temperature control.

The particle analysis system of the present invention, which includes a temperature control device and a pressure-balancing device as shown in FIG. 2, was used to sample $CF_4$ cylinder gas. The particle concentration in $CF_4$ cylinder gas at full pressure was measured with and without temperature control of the outflow gas for 30 minutes. The temperature setting was set at a predetermined temperature and the system was allowed to reach equilibrium at the intended sampling flow rate before actual sampling started. The results are shown in FIG. 3.

At ambient temperature, a particle level on the order of 5,000 particles/standard cubic foot ("scf") was registered in the outflow gas. These comparative results are indicated by the "no heating" data points shown in FIG. 3.

The particle level decreased to less than 10 particles/scf when the temperature of the outflow gas was maintained at 45° C. in accordance with the present invention. These results are indicated by the "heating" data points shown in FIG. 3.

EXAMPLE 3

Figure 4:
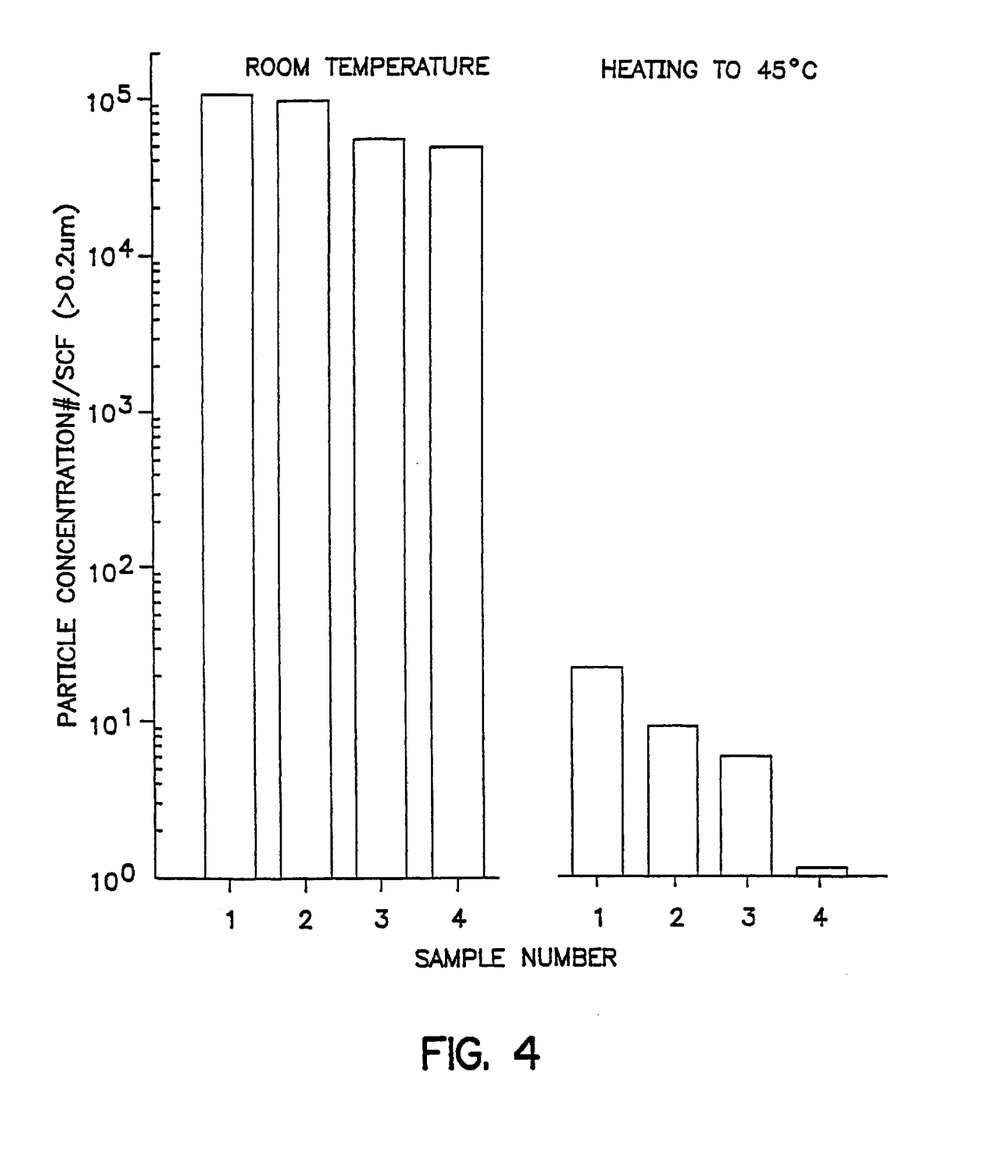
FIG. 4 is a graph exhibiting the relationship between the $CF_4$ particle concentration for four samples at ambient temperature and at 45° C.

The procedure of Example 2 was followed to sample $CF_4$ cylinder gas to verify the reproducibility of the method of the present invention. The results of four comparative samples at room temperature and four samples which were temperature controlled at 45° C. in accordance with the present invention are shown in FIG. 4. In each of the four samples, the particle counts were decreased by about four orders of magnitude when the temperature was controlled at 45° C. in accordance with the present invention.

EXAMPLE 4

Figure 5:
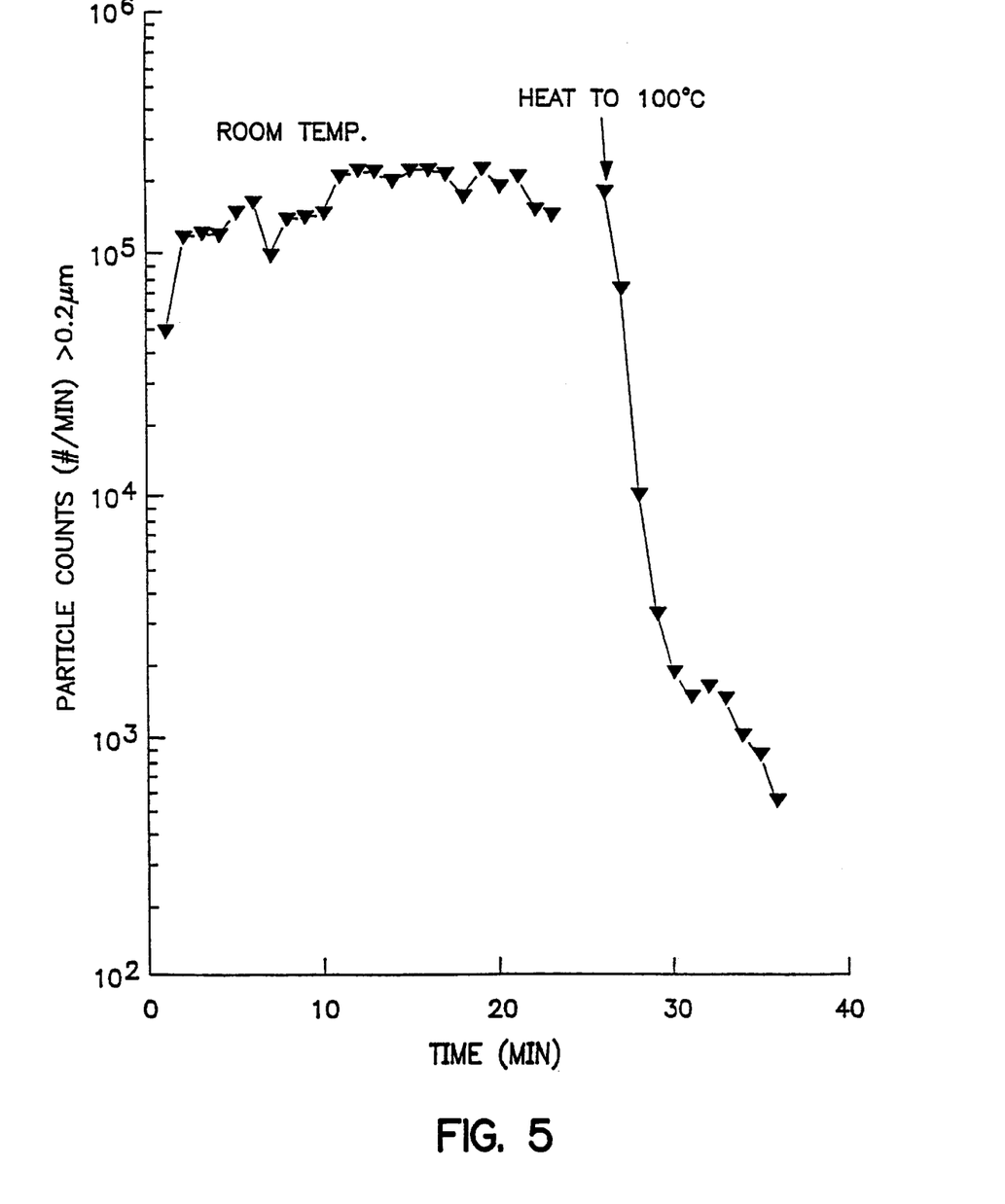
FIG. 5 is a graph exhibiting the relationship between the HCl particle concentration at full cylinder pressure over time with and without temperature control.

The procedure of Example 2 was followed to sample HCl cylinder gas in accordance with the method of the present invention. The temperature was controlled at 100° C. HCl was delivered in a cylinder as a liquid while the gaseous HCl in the head space was withdrawn for various applications. The particle concentration in HCl cylinder gas at full pressure was measured with and without temperature control of the outflow gas for 30 minutes. The temperature setting was set at a predetermined temperature and the system was allowed to reach equilibrium at the intended sampling flow rate before actual sampling started, The results are shown in FIG. 5.

At ambient temperature, a particle level on the order of 200,000 particles/minute was registered in the outflow gas. These comparative results are indicated by the "room temperature" data points shown in FIG. 5.

The particle level decreased to less than 1,000 particles/minute when the temperature of the outflow gas was maintained at 100° C. in accordance with the present invention. These results are indicated by the "heat to 100° C." data points shown in FIG. 5.

EXAMPLE 5

The method of the present invention was used for determining the optimum temperature setting for a given gas at various pressures. The optimum temperature setting is experimentally determined in the following manner. This method is general and can be applied for all gases compatible with the particle counter. An apparatus suitable in the method of the present invention is shown in FIG. 6.

The particle filter downstream of the pressure regulator removes all particles from the cylinder gas and from the flow handling components such as the cylinder valve and the pressure regulator. After proper purging, the sample gas is regulated and introduced through the filter into the Pressure Balance Temperature Control System while particles are counted. Starting from near ambient pressure, minimum counts are established. The pressure is then increased incrementally until the onset of additional particle counts occurs. At the onset pressure, the temperature is then increased incrementally. The increase of temperature is slow to allow equilibrium of the whole system. At each temperature, particle counts are recorded and follow a decaying trend with increasing temperature. The temperature setting for this pressure is the temperature at which particle counts reach a minimum. A further increase of pressure would require a further increase of the temperature setting to obtain minimum counts. By repeating this process, the temperature setting at each pressure can be established for a given gas.

The temperature setting depends on the type of gas, the cylinder pressure, and the withdrawn flow rate. The higher the flow rate, the higher the temperature setting that is required to evaporate the artifact particles. It should be determined individually as described above for each application, and preferably should not exceed 250° C.

What is claimed is:

1. A method for analyzing impurities in compressed gas comprising:
    (a) introducing a compressed gas into a system comprising a sensor for measuring particle concentration within the gas wherein said compressed gas is $N_2$, Ar, He, $Cl_2$, HCl, $BCl_3$, HBr, $SF_6$, $CF_4$, $C_2F_6$, $SiH_4$, $SiH_2Cl_2$, or $NH_3$,
    (b) balancing the pressure of said introduced gas to a desired value,
    (c) maintaining the temperature of said gas at a preferred value, and
    (d) sampling the gas for particle impurity content.

2. The method of claim 1, wherein a purge gas is introduced to said system prior to the initial introduction of said compressed gas.

3. The method of claim 2, wherein said purge gas is $N_2$, Ar or He.

4. The method of claim 1, wherein said preferred temperature value is a temperature which eliminates particle formation from molecular clustering and condensation of the gas.

5. A method for determining the optimum temperature for analyzing the impurity content of a compressed gas at a given pressure which comprises:
    introducing a source of compressed gas at a first pressure and a first temperature through a filter to a particle sensor
    monitoring the particle count of the gas; and
    increasing the temperature while monitoring the particle count until the particle count approaches a constant value, wherein the optimum temperature at said first pressure is the temperature at which the particle count reaches a constant value.

6. The method of claim 5, further comprising:
    introducing a source of compressed gas at a second pressure;
    monitoring the particle count of the gas; and
    incrementally increasing the temperature while monitoring the particle count until the particle count approaches a constant value, wherein the optimum temperature at said second pressure is the temperature at which the particle count reaches a constant value.

7. The method of claim 6, wherein said first pressure is lower than said second pressure.

8. The method of claim 5, wherein said compressed gas is $N_2$, Ar, He, $Cl_2$, HCl, $BCl_3$, HBr, $SF_6$, $CF_4$, $C_2F_6$, $SiH_4$, $SiH_2Cl_2$, or $NH_3$.

9. The method of claim 5, wherein a purge gas is introduced prior to the initial introduction of said compressed gas.

10. A method for analyzing impurities in compressed gas, comprising:
    (a) introducing a compressed gas into a system comprising a sensor for measuring particle concentration within the gas, wherein a purge gas is introduced to said system prior to the initial introduction of said compressed gas,
    (b) balancing the pressure of said introduced gas to a desired value,
    (c) maintaining the temperature of said gas at a preferred value, and
    (d) sampling the gas for particle impurity content.

11. The method of claim 10, wherein said purge gas is $N_2$, Ar or He.

12. The method of claim 10, wherein said preferred temperature value is a temperature which eliminates particle formation from molecular clustering and condensation of the gas.

13. The method of claim 10, wherein said compressed gas is $N_2$, Ar, He, $Cl_2$, HCl, $BCl_3$, HBr, $SF_6$, $CF_4$, $C_2F_6$, $SiH_4$, $SiH_2Cl_2$, or $NH_3$.

14. A method for analyzing impurities in compressed gas, comprising:
    (a) introducing a compressed gas into a system comprising a sensor for measuring particle concentration within the gas, wherein said compressed gas is $N_2$, Ar, He, $Cl_2$, HCl, $BCl_3$, HBr, $SF_6$, $CF_4$, $C_2F_6$, $SiH_4$, $SiH_2Cl_2$, or $NH_3$,
    (b) equalizing the pressure of said introduced gas to a desired value,
    (c) maintaining the temperature of said gas at a preferred value which is a temperature which eliminates particle formation from molecular clustering and condensation of the gas, and
    (d) sampling the gas for particle impurity content.

* * * * *